United States Patent
Olalde Rangel

(10) Patent No.: US 7,553,503 B2
(45) Date of Patent: Jun. 30, 2009

(54) PHYTO-NUTRACEUTICAL SYNERGISTIC COMPOSITION FOR PARKINSON'S DISEASE

(75) Inventor: Jose Angel Olalde Rangel, 519 Cleveland St., Suite 101, Clearwater, FL (US) 33755

(73) Assignee: Jose Angel Olalde Rangel, Clearwater, FL (US)

( * ) Notice: Subject to any disclaimer, the term of this patent is extended or adjusted under 35 U.S.C. 154(b) by 0 days.

(21) Appl. No.: 11/462,193

(22) Filed: Nov. 16, 2006

(65) Prior Publication Data

US 2008/0118583 A1    May 22, 2008

(51) Int. Cl.
| | |
|---|---|
| *A61K 36/481* | (2006.01) |
| *A61K 36/254* | (2006.01) |
| *A61K 36/16* | (2006.01) |
| *A61K 31/51* | (2006.01) |
| *A61K 31/355* | (2006.01) |

(52) U.S. Cl. .................. 424/728; 424/752; 514/276; 514/458

(58) Field of Classification Search .............. None
See application file for complete search history.

(56) References Cited

U.S. PATENT DOCUMENTS 6,733,797 B1 *   5/2004   Summers .................. 424/728

OTHER PUBLICATIONS http://www.mayoclinic.org/parkinsons-disease/treatment.html.*

* cited by examiner

*Primary Examiner*—Michael V. Meller
*Assistant Examiner*—Catheryne Chen

(57) ABSTRACT

A Phytoceutical composition for the prevention and treatment of Parkinson's disease is provided. A specific combination of extracts of plants and nutraceuticals is based on categorizing plants and nutraceuticals into one of three groups, Energy, Bio-Intelligence, and Organization. Such combination has synergistic effects, with minimal side effects.

1 Claim, No Drawings

PHYTO-NUTRACEUTICAL SYNERGISTIC COMPOSITION FOR PARKINSON'S DISEASE

PRIOR RELATED APPLICATIONS

Not applicable.

FEDERALLY SPONSORED RESEARCH STATEMENT

Not applicable.

REFERENCE TO MICROFICHE APPENDIX

Not applicable.

FIELD OF THE INVENTION

The invention relates to a phyto-nutraceutical formulation used to treat Parkinson's disease. The formulation is a particular combination of plants and nutraceuticals that have synergistic effect in combination. The principles for selecting the beneficial formulation are also provided.

BACKGROUND OF THE INVENTION

The academic study of medicinal plants for the treatment of diverse diseases has been nearly as pervasive as the study of Western medicines. The active principles from many traditional medicines have been extracted from plants, the curative agents identified and their mechanisms of action determined. Plant based medicines are typically well tolerated, with less severe side effects as well as a smaller range of side effects. In contrast, while synthetic drugs can be highly effective, their use is often hampered by severe side effects. Additionally, while synthetic pharmaceuticals are based upon single chemicals, many phytomedicines exert their beneficial effects through the additive or synergistic action of several chemical compounds acting at single or multiple target sites associated with a physiological process.

As pointed out by Tyler (1999), this synergistic or additive pharmacological effect can be beneficial by eliminating the problematic side effects associated with the predominance of a single xenobiotic compound in the body. In this respect, Kaufman et al. (1999) extensively documented how synergistic interactions underlie the effectiveness of a number of phytomedicines. This theme of multiple chemicals acting in an additive or synergistic manner likely has its origin in the functional role of secondary products in promoting plant survival. For example, in the role of secondary products as defense chemicals, a mixture of chemicals having additive or synergistic effects at multiple target sites would not only ensure effectiveness against a wide range of herbivores or pathogens but would also decrease the chances of these organisms developing resistance or adaptive responses (Kaufman et al., 1999; Wink, 1999). Conclusion: On one hand, synthetics may have the required efficacy for disease treatment; however this can be marred by severe side effects. On the other hand, despite the excellent medicinal qualities of many plants, they are individually insufficient to take chronic degenerative diseases into remission. However, there is mounting evidence which demonstrates that medical plants contain synergistic efficacy and/or side-effect neutralizing combinations (Gilani and Rahman, 2005). Thus, what are needed in the art are better treatment regimes providing sufficient efficacy with improved patient tolerance.

SUMMARY OF THE INVENTION

A number of known beneficial plants and tonics were classified according to their capacity to enhance the three main elements that support overall health: Energy (E), Bio-intelligence (I) and Organization (O). A synergistic effect is expected when all three categories of herbs (E, I, O) are included in a formulation, preferably at least two or three or four plants from each category. Thus, one embodiment of the invention provides the selection of a formulation according to these principles; additional formulations are being prepared and tested. Another embodiment of the invention provides an effective, natural composition for treating Parkinson's disorder and symptoms. The composition can be used alone, or can be combined with simultaneous use of one or more pharmaceutical compositions.

DETAILED DESCRIPTION OF THE INVENTION

"Pharmaceutically acceptable excipients" is used herein according to art accepted meanings, and includes those ingredients needed to formulate a medicine for mammalian use, including the use of gelatin capsules.

"Synergistic" or "synergy" is used herein to mean that the effect is more than its additive property. In preferred embodiments, the synergy is at least 1.5, 2, 5, or 10 fold.

By use of "plants," what is meant herein is that the plant (or that portion with medicinal activity) is used whole, ground, or as an extract. Also included are purified active ingredients and derivatives thereof. However, it is believed that the best efficacy of plants used herein is achieved with the use of the entire plant or its extracts, rather than with the use of isolated active ingredients.

Further, although plants are named here according to commonly used nomenclature, with improving taxonomy plants are often reclassified. Whenever a plant is referenced, it includes related species with similar active ingredients.

The following examples are illustrative only and should not serve to unduly limit the invention.

EXAMPLE 1

Plant Characteristics—Parkinson's Disease

Energy Enhancing Components.—

*Eleutherococcus* or *Acanthopanax* senticosus (Russian Ginseng, Siberian Ginseng, Eleuthero, Devil's Shrub, Buisson du Diable, Touch-me-not, Wild Pepper, Shigoka, Acantopanacis senticosus). Contains terpenoids (oleanolic acid), Eleutheroside A (daucosterol); Eleutheroside B (siringin); Eleutheroside B1 (isofraxidin); Eleutheroside B4 (sesamin); Eleutheroside D and E (heteroside siringoresinol); Eleutheroside C, G, I, K, L and M; phytosterols ($\beta$-sitosterol), polysaccharides (eleutherans), volatile oils, caffeic acid, coniferyl aldehyde, and sugars. *Eleutherococcus*, increases energy and vitality levels, improving physical and mental performance, and quality of life.

Increases the contribution of oxygen to muscles and allows for longer exercising and faster recovery. Prevents tiredness. The adaptogenic effects of the root of eleutherococcus are produced by metabolic regulation of energy, nucleic acids, and tissular proteins. Eleuthero improves the formation of glucose-6-phosphate. Glucose-6-phosphate oxidizes by the way of pentose, producing substrates for the biosynthesis of nucleic acids and proteins. On the other hand, it increases the activity of succinate dehydrogenase and of muscular malato dehydrogenase, enzymes that intervene in the cycle of tricarboxilic acids, generating ATP. The Eleutherosides B and E are responsible for this adaptogenic activity. Eleuthero has been shown to bind to gluco or mineralocorticoid receptors, and stimulate production of T-lymphocyte and natural killer cells (immune-stimulant activity). It has antioxidant activity as well as. Treatment with *Acanthopanax* senticosus resulted in prophylactic effects on induced Parkinsonian bradykinesia and catalepsy. Immunohistochemistical analysis showed that *Acanthopanax* provided cytoprotective effects against loss of dopamine cells. The present results suggest that it may be possible to use *Acanthopanax* senticosus for the prevention of nigral degenerative disorders, e.g., Parkinson's Disease with depression, caused by exposure to toxic substances (Fujikawa T, Miguchi S, Kanada N. *Acanthopanax* senticosus Harms as a prophylactic for MPTP-induced Parkinson's disease in rats. *J. Ethnopharmacol.* 2005; 97:375-81). Russian Ginseng contains at least 40 active ingredients.

*Panax ginseng* (Chinese ginseng, *panax*, ren shen, jintsam, ninjin, Asiatic ginseng, Japanese ginseng, Oriental ginseng, Korean red ginseng) The main active components are ginsenosides (protopanaxadiols and protopanaxatriols types) these have been shown to have a variety of beneficial effects, including anti-inflammatory and antioxidant effects. They also confer energizing properties because they increase ATP synthesis. Studies indicate that *Panax* enhances phagocytosis, NK lymphocytes cell activity, and the production of interferon; improves physical and mental performance in mice and rats; and increases resistance to exogenous stress factors. Ginseng possesses neurotrophic and neuroprotective properties, which may be useful in preventing various forms of neuronal cell loss including the nigrostriatal degeneration seen in Parkinson's disease.

Such treatment significantly and dramatically blocks tyrosine hydroxylase-positive cell loss in the substantia nigra and reduces the appearance of locomotor dysfunction (Van Kampen J, Robertson H, Hagg T. Neuroprotective actions of the ginseng extract G115 in two rodent models of Parkinson's disease. *Exp Neurol.* 2003; 184:521-9). Ginsenoside Rg1 was found to protect against substantia nigra neurons loss. Rg1 prevented Gluthation reduction and superoxide dismutase activation in substantia nigra. The antioxidant property of Rg1 along with the blocking of signaling cascade might contribute to the neuroprotective effect of ginsenoside Rg1 (Chen X C, Zhou Y C, Chen Y. Ginsenoside Rg1 reduces MPTP-induced substantia nigra neuron loss by suppressing oxidative stress. *Acta Pharmacol Sin.* 2005; 26:56-62). Ginsenoside Rg1 showed protective effect on apoptosis of nigral neurons and this effect may be attributable to reducing the expression of iNOS and inhibiting the activation of caspase-3 (Chen Y, Chen X C. Possible mechanisms of the protective effect of ginsenoside Rg1 on apoptosis in substantia nigra neurons. *Yao Xue Xue Bao.* 2002; 37:249-52). This phytomedicine provides at least 86 active principles.

*Rhodiola rosea* (Golden Root, Roseroot, Artic root) consists mainly of phenylpropanoids (rosavin, rosin, rosarin—all specific to *R. rosea*), phenylethanol derivatives (salidroside, rhodioloside, tyrosol), flavanoids (catechins, proanthocyanidines, rodiolin, rodionin, rodiosin, acetylrodalgin, tricin), monoterpenes (rosiridol, rosaridin), triterpenes (daucosterol, beta-sitosterol), and phenolic acids (chlorogenic, caffeic, hydroxycinnamic and gallic acid). There are many species of *Rhodiola*, but rosavins seem to be unique to *R. Rosea*, and it is the preferred species for this formulation. *Rhodiola* increases energy levels because it activates ATP synthesis and re-synthesis in mitochondria, stimulating reparative processes after intense exercise (Abidov M, Crendal F, Grachev S. Effect of extracts from *Rhodiola rosea* and *Rhodiola crenulata* (Crassulaceae) roots on ATP content in mitochondria of skeletal muscles. *Bull Exp Biol Med.* 2003; 136:585-7). Plant adaptogens are compounds that increase the ability of an organism to adapt to environmental factors and to avoid damage from such factors. The beneficial effects of multi-dose administration of adaptogens are mainly associated with the hypothalamic-pituitary-adrenal (HPA) axis, a part of the stress-system that is believed to play a primary role in the reactions of the body to repeated stress and adaptation. In contrast, the single dose application of adaptogens is important in situations that require a rapid response to tension or to a stressful situation. *R. rosea* is the most active of the adaptogens producing, within 30 min of administration, a stimulating effect that continues for at least 4-6 hours (Panossian A, Wagner H. Stimulating effect of adaptogens: an overview with particular reference to their efficacy following single dose administration. *Phytother Res.* 2005; 19:819-38). Prophylactic introduction of a Rhodiola Rosea extract prevents the ischemic brain damage development. This plant arrests the development of hyper- and hypoperfusion in cerebral circulation, weakens the postischemic hyperglycemic reaction, lowers oxygen extraction by cerebral tissues, suppresses lactate acidosis, promotes pyruvate participation in metabolic processes inhibits edema swelling, prevents the "calcium paradox" development, and decreases manifestations of the lipid peroxidation processes (Pogorelyi V E, Makarova L M. *Rhodiola rosea* extract for prophylaxis of ischemic cerebral circulation disorder. *Eksp Klin Farmakol.* 2002; 65:19-22). A clinical, randomized, controlled trial showed that *Rhodiola rosea* produces a statistically significant improvement in total mental performance, overall level of mental fatigue, involving complex perceptive and cognitive cerebral functions, such as associative thinking, short-term memory, calculation and ability of concentration, and speed of audio-visual perception (Darbinyan V, Kteyan A, Panossian A. *Rhodiola rosea* in stress induced fatigue—a double blind cross-over study of a standardized extract SHR-5 with a repeated low-dose regimen on the mental performance of healthy physicians during night duty. *Phytomedicine.* 2000; 7:365-71). A clinical, randomized, controlled trial showed that *Rhodiola rosea* produces a significant improvement in physical fitness, mental fatigue, neuro-motoric tests and general well-being. (Spasov A A, Wikman G K, Mandrikov V B. A double-blind, placebo-controlled pilot study of the stimulating and adaptogenic effect of *Rhodiola rosea* SHR-5 extract on the fatigue of students caused by stress during an examination period with a repeated low-dose regimen. *Phytomedicine.* 2000; 7:85-9). Rhodiola provides 28 active principles in a single therapeutic.

Schizandra chinensis (Schisandra spenenthera, Chinese magnolia vine fruit, also known as Wuweizi and Wurenchum). The major active principles of Schizandra are lignans called schizandrines. Schizandra increase activities of some enzymes that intervene in the oxidative phosphorylation. Schizandra chinensis effectively increases mental performance and physical working capacity in humans. (Panossian A, Wagner H. Stimulating effect of adaptogens: an overview with particular reference to their efficacy following single dose administration. Phytother Res. 2005; 19:819-38). Schizandrol A is one of the effective components in the dried fruit of Schizandra chinensis. Previous studies have found that schizandrol A exerts inhibitory effects on the central nervous system (CNS). Significant elevations of dopamine and its metabolite DOPAC (in striatum) and DA (in hypothalamus) were observed after administration of schizandrol A, but schizandrol A had no affinity for dopamine D1 and D2 receptors, serotonin receptors and alpha 1-,alpha 2-adrenergic receptors, and it did not affect the binding of dopamine to dopamine D1 or D2 receptors. These results indicate that the inhibition exerted by schizandrol A on the CNS may be related to the dopamine system (Zhang L, Niu X. Effects of schizandrol A on monoamine neurotransmitters in the central nervous system. Zhongguo Yi Xue Ke Xue Yuan Xue Bao. 1991; 13:13-6). Schizandrins B pretreatment produced a dose-dependent decrease in the extent of lipid peroxidation and an enhancement in glutathione antioxidant status in brain tissue. This result suggests the antioxidant potential of Schizandrins B in protecting against cerebral oxidative stress (Ko K M, Lam B Y. Schizandrins B protects against tert-butylhydroperoxide induced cerebral toxicity by enhancing glutathione antioxidant status in mouse brain. Mol Cell Biochem. 2002; 238: 181-6). Schisanhenol completely inhibited the peroxidative damages of brain mitochondria and membranes. The swelling and disintegration of brain mitochondria, as well as the reduction of brain membrane fluidity were also prevented. Schisanhenol significantly impeded production of MDA and loss of ATPase activity induced by reoxygenation following anoxia. Schisanhenol induced increase of cytosol glutathione-peroxidase of brain under the condition of reoxygenation following anoxia. The other compound Schizandrin also has similar activity. But its potency is weaker than that of Schisanhenol.

All these results indicate that Schisanhenol and Schizandrin have protective action against oxidative stress (Xue J Y, Liu G T, Wei H L. Antioxidant activity of two dibenzocyclooctene lignans on the aged and ischemic brain in rats. Free Radic Biol Med. 1992; 12:127-35). This plant provides at least 81 active principles in a single therapeutic.

Bio-Intelligence Modulators.—

*Astragalus membranaceus* (Huang-Qi, Huangqi) This plant contains three main types of active principles. Isoflavones, which act as anti-oxidants; astragalans which act as immune-stimulants and anti-inflammatory by stimulating the phagocytic activity of macrophages, of the cytotoxic response of T and NK lymphocytes and of the production and activity of interferon; and astragalosides which act as modulators of the hypothalamus-hypofisis-adrenal axis response. It also conveys antioxidative properties. The root of *Astragalus membranaceus* is a crude drug used widely in Oriental medicines. It is a major component of Ougi-Keishi-gomotsu-to, a traditional herbal medicine, used for neuropathic patients with abnormal sensations and neuropathic leg pain. It was shown to have inhibitory effects on lipid peroxidation and protein oxidative modification. Antioxidant increases superoxide dismutase and scavenges free radical (Toda S, Yase Y, Shirataki Y. Inhibitory effects of astragali radix, crude drug in Oriental medicines on lipid peroxidation and protein oxidative modification of mouse brain homogenate by copper. Phytother Res. 2000; 14:294-6). Astragaloside IV, an extract from *Astragalus membranaceus*, markedly and significantly reduced infarct volume. It also decreased the levels of malondialdehyde, an indicator of lipid peroxidation, and increased the levels of the antioxidant enzymes glutathione peroxidase and superoxide dismutase in ischemic tissues. These results provide the first evidence of a neuroprotective effect of Astragaloside IV in ischemic brain injury. The anti-infarction effect of Astragaloside IV may be derived at least in part from its antioxidant properties (Luo Y, Qin Z, Hong Z. Astragaloside IV protects against ischemic brain injury in a murine model of transient focal ischemia. Neurosci Lett. 2004; 363:218-23).

In another study, it was found that in anoxic circumstance in the Radix astragali group, the morphological changes were mild; the effluxes of LDH and $K^+$ were decreased cell survival number value increased as compared with those in the control group. It was suggested that Radix astragali could protect neurons against anoxic damages in anoxic circumstance (He X, Li C, Yu S. Protective effects of radix astragali against anoxic damages to in vitro cultured neurons. J Tongji Med. Univ. 2000; 20: 126-7). Astragalosides were found to ameliorate age-related alternations in both motor response and memory, and enhanced the deteriorated cellular immunity. They also have an anti-aging effect and the effect of delaying senility, which was related to its improvement of brain function and immunomodulatory effects (Lei H, Wang B, Li WP. Anti-aging effect of astragalosides and its mechanism of action. Acta Pharmacol Sin. 2003; 24:230-4). *Astragalus* offers at least 38 active principles in a single therapeutic.

*Ganoderma lucidum* (Reishi, also G. tsugae, G. valesiacum, G. oregonense, G. resinaceum, G. pfezfferi, G. oerstedli, and G. ahmadii) is an edible fungus containing bitter triterpenoids (ganoderic acid), β-D-glucan, coumarins, alkaloids and ergosterols. The main active principles of this mushroom are sterols and beta-proteoglucans which bestow anti-inflammatory and immune-modulating properties, because they increase the phagocytotic capacity of macrophages, and increase the production—and lifetime—of CD4 lymphocytes as well. The polysaccharide component with a branched (1→6)-beta-D-glucan moiety of *G. lucidum* (PS-G) has been reported to activate natural killer cells. Also data suggests that can effectively promote the activation and maturation of immature dendritic cells suggesting that *Ganoderma* may posses a potential in regulating immune responses. *Ganoderma* has neuroprotective effect for preventing dopaminergic neuron damage. *Ganoderma* treatment produces significantly less involuntary movement of the limbs. *Ganoderma* increases the levels of dopamine and DOPAC in the striatum and the number of surviving neurons in substantia nigra pars compacta (Zhu W W, Liu Z L, Xu H W. Effect of the oil from *Ganoderma lucidum* spores on pathological changes in the substantia nigra and behaviors of MPTP-treated mice. Di Yi Jun Yi Da Xue Xue Bao. 2005; 25:667-71). *Ganoderma* clinically improves symptoms in neurasthenia.

A clinical, multicenter, Randomized Controlled Trial in 123 patients treated with *Ganoderma* extracts showed significantly better scores in the Clinical Global Impression severity score and sense of fatigue. Sense of well-being increased. (Tang W, Gao Y, Chen G. A randomized, double-blind and placebo-controlled study of a *Ganoderma lucidum* polysaccharide extract in neurasthenia. J Med. Food. 2005; 8:53-8). *Ganoderma* total sterol increases neuron viability. It also significantly reduces malondialdehyde content and reactive oxygen species production and increases manganese superoxide dismutase (Mn-SOD) activity; furthermore, the translocation of nuclear factor-kappa B and the production of interleukin-1beta and tumor necrosis factor alpha induced by hypoxia/reoxygenation is blocked, suggesting that *Ganoderma* total sterol might be useful in treating hypoxia/reoxygenation-induced oxidative stress and inflammatory responses. Reactive oxygen species (ROS), such as superoxide anions and hydroxyl radicals, are associated with carcinogenesis and other pathophysiological conditions. Therefore, elimination or inactivation of ROS or inhibition of their excess generation may be beneficial in terms of reducing the risk for cancer and other diseases. *Ganoderma lucidum* has been used in traditional oriental medicine and has potential anti-inflammatory and antioxidant activities. The amino-polysaccharide fraction from *Ganoderma lucidum* protects against oxidative damage induced by Reactive oxygen species. Significantly inhibits lipid peroxidation in brain and shows inactivation of hydroxyl radicals and superoxide anions (Lee J M, Kwon H, Jeong H. Inhibition of lipid peroxidation and oxidative DNA damage by *Ganoderma lucidum*. Phytother Res. 2001; 15:245-9). *Ganoderma* contains at least 32 active principles.

Uncaria tomentosa (Cat's Claw, Peruvian Cat's Claw, Samento, Saventaro, Uña de Gato, also Uncaria guianensis) has several alkaloids including pentacyclic oxindol alkaloids (POA) (isomitraphylline, isopteropodine, mitraphylline, pteropodine, speciophylline, uncarine F), tetracyclic oxindol alkaloids (TOA) (isorynchophylline, rynchophylline), glycosides (triterpenic quinovic acid glycosides), hirsutine, tannins, catechins, phytosterols (beta-sitosterol, campesterol, stigmasterol), triterpenes, polyphenols, flavanols and oligomeric proanthocyanidins (OPC).

It is an immune-stimulant, an anti-inflammatory, vasodilator, and antioxidant. Uncaria tomentosa offers high antioxidant activity in comparison to the other extracts of fruits, vegetables, cereals and medicinal plants. This activity is explained by high peroxyl radical-trapping capacity and superoxide radical scavenging activity (Pilarski R, Zielinski H, Ciesiolka D. Antioxidant activity of ethanolic and aqueous extracts of Uncaria tomentosa (Willd.) DC. J. Ethnopharmacol. 2006; 104:18-23). Uncaria presents a potent radical scavenger activity, as suggested by its high capacity to reduce free radicals, and by its reaction with superoxide anion, peroxyl and hydroxyl radicals as well as with the oxidant species, hydrogen peroxide and hypochlorous acid. It also protected membrane lipids against peroxidation (Goncalves C, Dinis T, Batista M T. Antioxidant properties of proanthocyanidins of Uncaria tomentosa bark decoction: a mechanism for anti-inflammatory activity. Phytochemistry. 2005; 66:89-98). A Clinical Randomized Controlled Trial showed a statistically significant decrease of DNA damage and a concomitant increase of DNA repair in the Uncaria tomentosa supplement groups when compared with non-supplemented controls (Sheng Y, Li L, Holmgren K. DNA repair enhancement of aqueous extracts of Uncaria tomentosa in a human volunteer study. Phytomedicine. 2001; 8:275-82). This phytomedicine provides at least 29 active ingredients.

Organizational Improvers.—

Coenzyme Q10 (CoQ10), also known as ubiquinone or ubiquinol, is a biologically active quinone with an isoprenoid side chain, related in structure to vitamin K and vitamin E. CoQ is found in the membranes of endoplasmic reticulum, peroxisomes, lysosomes, vesicles and notably the inner membrane of the mitochondrion where it is an important part of the electron transport chain; there it passes reducing equivalents to acceptors such as Coenzyme Q—cytochrome c reductase: $CoQH_2+2\ Fe^{+3}$-cytochrome $c \rightarrow CoQ^{+2}Fe^{+2}$-cytochrome c CoQ is also essential in the formation of the apoptosome along with other adapter proteins. The loss of trophic factors activates pro-apoptotic enzymes, causing the breakdown of mitochondria. Because of its ability to transfer electrons and therefore act as an antioxidant, Coenzyme Q has become a valued dietary supplement. Young people are able to make Q10 from the lower numbered ubiquinones such as Q6 or Q8.

The sick and elderly may not be able to make enough, thus Q10 becomes a vitamin later in life and in illness. Supplementation of Coenzyme Q10 has been found to have a beneficial effect on the condition of some sufferers of migraine headaches, and is a common component of the 'mito cocktail' used to treat mitochondrial disorders and other metabolic disorders. Recent studies have shown that the antioxidant properties of Coenzyme Q10 benefit the body and the brain. Some of these studies indicate that Coenzyme Q10 protects the brain from neurodegenerative disease such as Parkinson's and also from the damaging side effects of a transient ischemic attack (stroke) in the brain. Results of the first placebo-controlled, multicenter clinical trial of the compound coenzyme Q10 suggest that it can slow disease progression in patients with early-stage Parkinson's disease. These results provide hope that this compound may ultimately provide a new way of treating Parkinson's disease. The phase II study, led by Clifford Shults, M.D., of the University of California, San Diego (UCSD) School of Medicine, looked at a total of 80 PD patients at 10 centers across the country to determine if coenzyme Q10 is safe and if it can slow the rate of functional decline. The study was funded by the National Institute of Neurological Disorders and Stroke (NINDS) and appears in the Oct. 15, 2002, issue of the Archives of Neurology (Shults C W, Oakes D, Kieburtz K. and the Parkinson Study Group. Effects of coenzyme Q10 in early Parkinson disease: evidence of slowing of the functional decline. Archives of Neurology, 2002, Vol. 59, No. 10, pp. 1541-1550.

*Ginkgo biloba* (*Ginkgo*) contains ginkgolides, bilobalides, bioflavones and flavone glycosides. Flavone glycosides include quercetin, 3-methylquercetin and kaempferol. Quercetin, myrcetin and the rest of the flavonoid fraction of the extract have antioxidant and free radical scavenger effects. Flavonoids diminish infiltration by neutrophils and increase blood flow. Their antioxidant properties and membrane stabilizing activity increase the tolerance to hypoxia. They improve cellular metabolism and protect against damage caused by ischemia. Ginkgolide B is a powerful PAF inhibitor, which bonds to membrane receptors and is an antagonist of platelet aggregation. It also has anti-inflammatory properties by reducing vascular permeability and has vasodilator effects by inhibiting the liberation of thromboxane A2 and prostaglandins.

Controlled double blind clinical studies conclusively demonstrate the effectiveness of *Gingko biloba* in treating arterial insufficiency. In a recent study the administration of gingko during 3 months significantly reduced malonaldehide levels in the erythrocyte membranes, diminished the fibrinogen levels, and improved the viscosity and visco-elasticety of the blood, which facilitated blood perfusion. Gingko improved the brains' function, stimulating the anti-oxidative defenses, diminishing the lipidic peroxidation rate, which reduces neuronal damage. Increases blood flow and improves functions. *Ginkgo biloba* extract, a potent antioxidant, was evaluated for its anti-parkinsonian effects. The increase in rotations and deficits in locomotor activity and muscular coordination were significantly restored. *Ginkgo biloba* extract diminished the generation of thiobarbituric acid reactive substances and increased the glutathione content in substantia nigra. It also restored the activities of glutathione-dependent enzymes, catalase, and superoxide dismutase in striatum. *Ginkgo* significantly recovered the level of dopamine and its metabolites and the number of dopaminergic D2 receptors in striatum. It also increased the density of tyrosine hydroxylase-immunoreactive fibers in the ipsilateral substantia nigra of the lesioned group; the lesioning had induced almost a complete loss of tyrosine hydroxylase-immunoreactive fibers. It can be concluded that EGb can be used as a therapeutic approach to check the neuronal loss following parkinsonism (Ahmad M, Saleem S, Ahmad A S. *Ginkgo biloba* affords dose-dependent protection against 6-hydroxydopamine-induced parkinsonism in rats: neurobehavioral, neurochemical and immunohistochemical evidences. J. Neurochem. 2005; 93:94-104). *Ginkgo biloba* may also decrease the toxicity of levodopa. The combined use of *Ginkgo biloba* with Levodopa may be a workable method to treat Parkinson Disease and may be better than using Levodopa alone. (Cao F, Sun S, Tong E T. Experimental study on inhibition of neuronal toxic effect of levodopa by *ginkgo biloba* extract on Parkinson disease in rats. J Huazhong Univ Sci Technolog Med. Sci. 2003; 23:151-3). There is considerable evidence suggesting that mitochondrial dysfunction and oxidative damage may play a role in the pathogenesis of Parkinson's disease. There is substantial evidence that mitochondria are a major source of free radicals within the cell.

Several agents can modulate cellular energy metabolism and that may exert antioxidative effects. Agents that have shown to be beneficial in animal models of Parkinson's disease include coenzyme Q10 and *Ginkgo biloba*. Coenzyme Q10 is also effective in animal models and has shown promising effects both in clinical trials of Parkinson's disease as well as in clinical trials in Huntington's disease and Friedreich's ataxia. These agents therefore are promising candidates for further study as neuroprotective agents in Parkinson's disease (Beal M F. Bioenergetic approaches for neuroprotection in Parkinson's disease. Ann Neurol. 2003; 53:S39-47; discussion S47-8). The neuroprotective effect of widely used cognition-enhancing drugs, such as the extract of *Gingko biloba*, may also be a result of their interaction with mitochondria (Shevtsova E F, Kireeva E G, Bachurin S O. Mitochondria as the target for neuroprotectors. Vestn Ross Akad Med. Nauk. 2005; 13-7). The neuroprotective effects of *Gingko biloba* reduce the behavioral deficit and also indicate a possible role for the extract in the treatment of Parkinson's disease (Kim M S, Lee J I, Lee W Y. Neuroprotective effect of *Ginkgo biloba* L. extract in a rat model of Parkinson's disease. Phytother Res. 2004; 18:663-6). Numerous studies have shown that *Ginkgo* has antioxidant and neuroprotective properties and utility in cerebrovascular insufficiency and impaired cerebral performance. *G. biloba* extract restored restraint stress-induced elevation in whole brain levels of catecholamines (NE, DA) 5-HT and plasma corticosterone to near normal levels (Shah Z A, Sharma P, Vohora S B. *Ginkgo biloba* normalizes stress-elevated alterations in brain catecholamines, serotonin and plasma corticosterone levels. Eur Neuropsychopharmacol. 2003; 13:321-5). *Ginkgo biloba* possesses protective effect on the Parkinson Disease models in vivo and in vitro. The anti-oxidation and anti-apoptosis may be one of the mechanisms underlying the neuroprotective effect of Ginkgo (Yang S F, Wu Q, Sun A S. Protective effect and mechanism of *Ginkgo biloba* leaf extracts for Parkinson disease induced by 1-methyl-4-phenyl-1,2,3,6-tetrahydropyridine. Acta Pharmacol Sin. 2001; 22:1089-93). *Ginkgo biloba* appears to display neuroprotective effect in many nervous diseases and aging. *Ginkgo* provides 59 active principles.

Hydrocotile asiatica (Gotu Kola, Bramhi, Pennywort, Marsh Penny, Pennywort and Centella asiatica) contains terpenoids (asiaticoside, brahmoside and brahminoside), aglycones (saponin glycosides), asiaticentoic acid, centellic acid, centoic acid and madecassic acid, sesquiterpenes (caryophyllene, trans-B-farnesene), volatile oils (Germacrene D), alkaloids (hydrocotylin), flavonoids (Quercetin, kaempferol), phytosterols (stigmasterol and sitosterol), and vallerine, fatty acids, resin, and tannins. Centella asiatica showed a significant protective action on inhibited blood delta-aminolevulinic acid dehydratase activity and restored the blood glutathione level. A significant protection observed in brain thiobarbituric acid reactive substance (Gupta R, Flora S J. Effect of Centella asiatica on arsenic induced oxidative stress and metal distribution in rats. J Appl Toxicol. 2006; 26:213-22). Significant reduction of the corticosterone level in serum and increase of the contents of 5-HT, NE, DA and their metabolites 5-HIAA, MHPG in rat brain were observed. The antidepressant effect of total triterpenes of Centella asiatica may be involved in ameliorating the function of HPA axis and increasing the contents of monoamine neurotransmitters (Chen Y, Han T, Rui Y. Effects of total triterpenes of Centella asiatica on the corticosterone levels in serum and contents of monoamine in depression rat brain. Zhong Yao Cai. 2005; 28:492-6). Free radicals play an important role in ageing process. There exists an imbalance between free radical production and antioxidant defense mechanism, which may lead to cell death during ageing. Supplementation of C. asiatica was effective in reducing brain regional lipid peroxidation and protein carbonyl levels and in increasing the antioxidant status. Thus, C. asiatica by acting as a potent antioxidant exerted significant neuroprotective effect and proved efficacious in protecting rat brain against age related oxidative damage (Subathra M, Shila S, Devi M A. Emerging role of Centella asiatica in improving age-related neurological antioxidant status. Exp Gerontol. 2005; 40:707-15). The total triterpenes from Centella asiatica show antidepressant activity (Chen Y, Han T, Qin L Effect of total triterpenes from Centella asiatica on the depression behavior and concentration of amino acid in forced swimming mice. Zhong Yao Cai. 2003; 26:870-3). Centella asiatica has been described as possessing central nervous system activity, such as improving intelligence.

Studies have demonstrated that C. asiatica has cognitive-enhancing and anti-oxidant properties in normal rats. Oxidative stress or an impaired endogenous anti-oxidant mechanism is an important factor that has been implicated in Alzheimer's disease and cognitive deficits seen in the elderly. C. asiatica increased cognitive behavior; significantly decreased MDA and increased glutathione and catalase levels. C. asiatica is effective in preventing the cognitive deficits, as well as the oxidative stress (Veerendra Kumar M H, Gupta Y K. Effect of Centella asiatica on cognition and oxidative stress in an intracerebroventricular streptozotocin model of Alzheimer's disease in rats. Clin Exp Pharmacol Physiol. 2003; 30:336-42). Centella has cognitive enhancing effect, an antioxidant mechanism is involved (Veerendra Kumar M H, Gupta Y K. Effect of different extracts of Centella asiatica on cognition and markers of oxidative stress in rats. J. Ethnopharmacol. 2002; 79:253-60). This plant provides at least 59 active principles in a single therapeutic.

Tabebuia avellanedae (Pau d'arco, Ipê, Lapacho, Tahuari, Taheebo, Trumpet Tree, Tabebuia Ipê, Tajy; also T. ipe, T. nicaraguensis, T. schunkeuigoi, T. serratifolia, T. altissima, T. palmeri, T. impetiginosa, T. heptaphylla, Gelseminum avellanedae, Handroanthus avellanedae, H. impetiginosus, Tecoma adenophylla, Tec. avellanedae, Tec. eximia, Tec. impetiginosa, Tec. integra, Tec. ipe) extracts contain diverse quinone derivatives and a small quantity of benzenoids and flavonoids, including beta-lapachone, xyloidone, tabebuin, quercetin, tecomine, and steroidal saponins. One important ingredient is lapachol, a derivative of which was patented in 1975. It has anti-inflammatory and antibacterial effects. Some evidence suggests a possible deleterious effect of neuroinflammatory processes caused by infections in Parkinson's disease (Arai H, Furuya T, Mizuno Y. Inflammation and infection in Parkinson's disease. Histol Histopathol. 2006; 21:673-8). Rifampicin, an antibiotic is surprisingly effective against Parkinson's disease; this would suggest an infectious origin in Parkinson. (Bradbury J. New hope for mechanism-based treatment of Parkinson's disease. Drug Discov Today. 2005; 10:80-1). One randomized, double-blind, placebo-controlled efficacy study points to a direct or surrogate (not necessarily unique) role of *Helicobacter pylori* infection in the pathogenesis of Parkinsonism (Bjarnason I T, Charlett A, Dobbs R J. Role of chronic infection and inflammation in the gastrointestinal tract in the etiology and pathogenesis of idiopathic parkinsonism. Part 2: response of facets of clinical idiopathic parkinsonism to *Helicobacter pylori* eradication. A randomized, double-blind, placebo-controlled efficacy study. *Helicobacter.* 2005; 10:276-87). The biologically active components of Tabebuia impetiginosa dried inner bark exhibit strong activity against *Helicobacter pylori* (Park B S, Lee H K, Lee S E. Antibacterial activity of Tabebuia impetiginosa Martius ex DC (Taheebo) against *Helicobacter pylori*. J. Ethnopharmacol. 2006; 105:255-62). Streptococcal infection should be considered in the differential diagnosis of all acute onset movement disorders (McKee D H, Sussman J D. Case report: severe acute Parkinsonism associated with streptococcal infection and antibasal ganglia antibodies. Mov Disord. 2005; 20:1661-3). Brain viral infections and immune activation may be causative of the neuronal loss in Parkinson's disease (Ringheim G E, Conant K. Neurodegenerative disease and the neuroimmune axis—Alzheimer's and Parkinson's disease, and viral infections)—J. Neuroimmunol. 2004; 147:43-9); (Takahashi M, Yamada T. Viral etiology for Parkinson's disease—a possible role of influenza A virus infection. Jpn J Infect Dis. 1999; 52:89-98). Active principles in Tabebuia exhibited inhibitory effects on Epstein-Barr virus early antigen (EBV-EA) activation (Sacau E P, Estevez-Braun A, Ravelo A G. Inhibitory effects of lapachol derivatives on Epstein-Barr virus activation. Bioorg Med. Chem. 2003; 11:483-8). Naphthoquinones structurally related to lapachol showed significant effects against proliferation of Herpes Simplex Virus type 2 infections (da Silva A J, Buarque C D, Brito F V. Synthesis and preliminary pharmacological evaluation of new (+/−) 1.4-naphthoquinones structurally related to lapachol. Bioorg Med. Chem. 2002; 10:2731-8). Beta-lapachone is a potent and selective inhibitor of HIV-1 viral long terminal repeat-directed gene expression. Tabebuia provides 32 active principles.

Silybum marianum (Carduus marianus, Holy thistle, Marian thistle, and Mary thistle) The main active principles are: flavonolignans, including Silibine, Silibinin, Silicristine, Isosilibinin and Silidianin, collectively known as Sylimarin. This compound has the highest grade of anti-inflammatory activity. Mechanisms which explain its therapeutic properties are diverse and include: anti-oxidation; lipidic anti-peroxidation; improvement in detox capacity through a competitive inhibition with toxic substances; and protection against glutathione depletion. Anti-inflammatory effects are due to mastocytes stabilization, inhibition of neutrophils, and strong inhibition of leucotrien and prostaglandin formation. An inflammatory response in the central nervous system mediated by activation of microglia is a key event in the early stages of the development of neurodegenerative diseases. Silymarin has anti-inflammatory and cytoprotective effects. Silymarin significantly inhibits the LPS-induced activation of microglia and the production of inflammatory mediators, such as tumor necrosis factor-alpha and nitric oxide, and reduces the damage to dopaminergic neurons. Silymarin significantly reduced the LPS-induced nitrite, inducible nitric oxide synthase mRNA and protein levels. Silymarin effectively reduces LPS-induced superoxide generation and nuclear factor kappaB (NF-kappaB) activation (Wang M J, Lin W W, Chen H L. Silymarin protects dopaminergic neurons against lipopolysaccharide-induced neurotoxicity by inhibiting microglia activation. Eur J. Neurosci. 2002; 16:2103-12). The incorporation of Silybum provides at least 57 active principles in a single therapeutic.

Smilax regelii (S. ornate, S. aristolochiaefolia, S. febrifiga, S. ovalifolia, S. lancaefolia) The main active principles are fitosterols (sitosterols β and ε, stigmasterol, sitosterol-d-glucoside) and steroid saponins (sarsasapogenin, sarsaponin, smilagenin, diosgenine, tigogenin, asparagines, laxogenin) Flavonoids (quercetin and kaempferol) and minerals (Al, Cr, Co, P, Fe, Mg, Mn, K, Se, Si, Zn). Smilax has various pharmacological effects including anti-inflammatory and antioxidant activity. Smilax prevents neuronal cell damage: inhibits neuronal cell death, elevation of cytosolic calcium concentration, glutamate release, generation of reactive oxygen species and activation of caspase-3 (Ban J Y, Cho S O, Koh S B. Protection of amyloid beta protein (25-35)-induced neurotoxicity by methanol extract of Smilacis chinae rhizome in cultured rat cortical neurons. J. Ethnopharmacol. 2006; 106:230-7). Smilax regelii provides at least 35 active principles in a single therapeutic.

Radix Polygalae (*Polygala tenuifolia, Polygala sibirica,* Chinese Senega, *Polygala fallax, Polygala caudata, Polygala paniculata*). Active principles: Xanthones, Oleanane-type Triterpenoid saponins (Polygalasaponins, Onjisaponins, Reiniosides, Tenuifolin, Tenuidin, Tenuigenin, Presenegenin, Senegenin, Senegasaponins and senegins); Phytosterols (Daucosterol), oligosaccharide esters (Senegoses A-E, Tenuifoliose Q); phenolic compounds (polygalolides A-B) and fatty acids (oleic acid, linoleic acid, palmitic acid, eicosenoic acid and stearic acid). In vitro studies showed that polygalasaponins from *Polygala tenuifolia* have an affinity for both dopamine and serotonin receptors (Chung I W, Kim Y S, Ahn J S, Pharmacologic profile of natural products used to treat psychotic illnesses. Psychopharmacol Bull. 1995; 31:139-45). This root can reduce brain damage during ischemia and reperfusion; prevent lipid peroxidation and preserve the energy metabolism (Park J H, Kim J S, Jang D S. Effect of *Polygala tenuifolia* root extract on cerebral ischemia and reperfusion. Am J Chin Med. 2006; 34:115-23). *Polygala paniculata* extract offers protective effects against neurotoxicity. Improves glutathione peroxidase activity, reduces free radical substances levels and recovers deficit in motor performance (Lin LLFarina M, Franco J L, Ribas C M. Protective effects of *Polygala* paniculata extract against methylmercury-induced neurotoxicity in mice. J Pharm Pharmacol. 2005; 57: 1503-8). Xanthones of *Polygala* show different anti-oxidation activities: scavenger activity of the reactive oxygen free radicals (Lin L L, Huang F, Chen S B. Chemical constituents in roots of *Polygala fallax* and their anti-oxidation activities in vitro. Zhongguo Zhong Yao Za Zhi. 2005; 30:827-30); (Lin L L, Huang F, Chen S B. Xanthones from the roots of *Polygala caudata* and their antioxidation and vasodilatation activities in vitro. Planta Med. 2005; 71:372-5). *P. tenuifolia* could significantly reverse cognitive impairments. It significantly reduced cell death, amyloid beta protein and C-terminal fragment of amyloid precursor protein. In addition, inhibited acetylcholinesterase activity. This extract may have some protective effects against neuronal death and cognitive impairments in Alzheimer's disease and other neurodegenerative diseases related to excitotoxicity and central cholinergic dysfunction (Park C H, Choi S H, Koo J W. Novel cognitive improving and neuroprotective activities of *Polygala tenuifolia* Willdenow extract, BT-11. J Neurosci Res. 2002; 70:484-92). Radix polygalae provides 31 active principles.

Vitamin E A systematic review and meta-analysis of observational studies found that dietary intake of vitamin E protects against Parkinson's Disease. The protective influence was seen with both moderate and high intake of vitamin E. The meta-analysis concludes that dietary vitamin E may have a neuroprotective effect attenuating the risk of Parkinson's Disease (Etminan M, Gill S S, Samii A. Intake of vitamin E, vitamin C, and carothenoids and the risk of Parkinson's disease: a meta-analysis. Lancet Neurol. 2005; 4:362-5). New experimental data are presented that supports the enrichment of mitochondria with d-alpha-tocopherol as a critical event in cytoprotection against toxic mitochondria-derived oxidative stress. Chronic, high dose vitamin E dietary supplementation or parenteral vitamin E administration may serve as a successful therapeutic strategy for the prevention or treatment of Parkinson Disease (by enriching substantia nigra mitochondria with protective levels of d-alpha-tocopherol) (Fariss M W, Zhang J G. Vitamin E therapy in Parkinson's disease. Toxicology. 2003; 189:129-46). Inflammatory processes and vascular dysfunctions appear to play important roles in the pathogenesis of age-associated pathologies including Parkinson's disease. A large body of evidence shows that both vitamins E and C are important for the central nervous system and that a decrease in their concentrations causes structural and functional damage to the cells. Several studies reveal a link between diets rich in fruits and vegetables containing generous amounts of vitamins E and C and lower incidence of certain chronic diseases (Martin A, Youdim K, Szprengiel A. Roles of vitamins E and C on neurodegenerative diseases and cognitive performance. Nutr Rev. 2002; 60:308-26). Oxidative damage has been implicated in the pathogenesis of Parkinson's Disease. The risk of PD was significantly reduced among men and women with high intake of dietary vitamin E—from foods only—(Zhang S M, Hernan M A, Chen H. Intakes of vitamins E and C, carothenoids, vitamin supplements, and PD risk. Neurology. 2002; 59:1161-9. It seems that alpha-tocopherol may be an effective drug in the early initial stages of the disease (Heim C, Kolasiewicz W, Kurz T. Behavioral alterations after unilateral 6-hydroxydopamine lesions of the striatum. Effect of alpha-tocopherol. Pol J. Pharmacol. 2001; 53:435-48). There is strong evidence that oxidative stress participates in the etiology of Parkinson's disease (PD). Repeated intramuscular administration of vitamin E exerts a rapid protective effect on the nigrostriatal dopaminergic neurons in the early unilateral model of PD (Roghani M, Behzadi G. Neuroprotective effect of vitamin E on the early model of Parkinson's disease in rat: behavioral and histochemical evidence. Brain Res. 2001; 892:211-7). Data suggest that a high intake of dietary vitamin E may protect against the occurrence of PD (de Rijk M C, Breteler M M, den Breeijen J H. Dietary antioxidants and Parkinson disease. The Rotterdam Study. Arch Neurol. 1997; 54:762-5). A Clinical Randomized Controlled Trial reported that Vitamin E appears to be effective in reducing the severity of tardive dyskinesia, especially in patients who have had tardive dyskinesia for 5 years or less. (Lohr J B, Caligiuri M P. A double-blind placebo-controlled study of vitamin E treatment of tardive dyskinesia. J Clin Psychiatry. 1996; 57:167-73). Severe and prolonged vitamin E deficiency results in loss of nigrostriatal nerve terminals, and supports the hypothesis that oxidative stress may contribute to the etiology of Parkinson's disease. (Dexter D T, Brooks D J, Harding A E. Nigrostriatal function in vitamin E deficiency: clinical, experimental, and positron emission tomographic studies. Ann Neurol. 1994; 35:298-303).

Vitamin B1 It helps maintain the correct nervous systems' function. Systemic thiamine deficiency can lead to a myriad of problems including Parkinson's Disease. Thiamine is an essential co-factor for several important enzymes involved in brain oxidative metabolism, such as the alpha-ketoglutarate dehydrogenase complex (KGDHC), pyruvate-dehydrogenase complex, and transketolase. The activity of KGDHC is decreased in the substantia nigra or patients with Parkinson's disease (PD). Lower CSF free thiamine levels in the PD-patient group. These results suggest that low CSF free thiamine levels could be related with the risk for PD (Jimenez-Jimenez F J, Molina J A, Hernanz A. Cerebrospinal fluid levels of thiamine in patients with Parkinson's disease. Neurosci Lett. 1999; 271:33-6). Thiamine deficiency decreased the dopamine (DA) concentration of the striatum indicating a reduced DA synthesis. (Sjoquist B, Johnson H A, Neri A. The influence of thiamine deficiency and ethanol on rat brain catecholamines. Drug Alcohol Depend. 1988; 22:187-93). Thiamin deficiency diminishes motor performance. Alterations of Dopamine accompany thiamin deficiency. (Freeman G B, Gibson G E. Dopamine, acetylcholine, and glutamate interactions in aging. Behavioral and neurochemical correlates. Ann N Y Acad. Sci. 1988; 515:191-202).

EXAMPLE 2

Composition_Parkinsons' Disease

A particularly preferred composition is shown in Table 1. Ratios reflect the concentration of active ingredient over the natural state, and the amounts provided are mg of extract. Obviously, the amount should be increased where the strength is reduced, and vice versa. A particularly preferred composition is shown in Table 1.

TABLE 1

| Active Agent | Ratio | Amount (mg) |
|---|---|---|
| Energy enhancers | | |
| Eleutherococcus senticosus | 5:1 | 21 |
| Panax ginseng | 5:1 | 106 |
| Rhodiola rosea | 10:1 | 32 |
| Schizandra chinensis | 5:1 | 4 |
| Bio-Intelligence modulators | | |
| Astragalus membranaceus | 10:1 | 106 |
| Ganoderma lucidum | 5:1 | 106 |
| Uncaria tomentosa | 5:1 | 106 |
| Organization improvers | | |
| Coenzime Q10 | 1:1 | 21 |
| Ginkgo bilova | 50:1 | 21 |
| Hydrocotile asiatica | 5:1 | 64 |
| Radix polygalae | 5:1 | 106 |
| Silybum marianum | 5:1 | 21 |
| Smilax regelii | 5:1 | 4 |
| Tabebuia avellanedae | 5:1 | 21 |
| Vitamin B1 | 1:1 | 106 |
| Vitamin E | 1:1 | 106 |
| Total | | 951 |

EXAMPLE 3

Parkinson's Disease Effectiveness and Tolerance

The effects of Parkinson's synergistic phytoceutical composition, a pathology targeted phyto-nutraceutical therapy formulated under the precepts of Systemic Medicine, were evaluated in 80 patients with Parkinson's disease, through a retrospective, multicenter, descriptive, two year long study. Systemic treatment improved the tremor in 74.65% of the patients, muscle rigidity in 70.21%, slow movements in 60.61%; voice or speech changes in 85.71% and autonomic disturbances in 67.44% of the patients. Also, a significant improvement in all of the Quality of life indicators, such as: physical and mental wellbeing (70%), appetite (61.25%), more energy levels (88.75%), adequate sleep (86.25%) and evacuations (82.5%). Tolerance results were outstanding, without adverse effects. It is important to acknowledge that conventional treatments diminish effectiveness in time and cause adverse effects. This formulation is an extraordinary treatment for Parkinson's disease patients and should be considered as an essential part of their treatment.

EXAMPLE 4

Principles for Selecting Synergistic Combinations

In order to explain the range of formulations encompassed by the invention, we have categorized beneficial plants and nutraceuticals into one of three groups, each of which should be present for synergistic effect. The classifications are: Energy, Bio-Intelligence and Organization. Plants and nutraceuticals classified under Energy are associated with ATP synthesis (such as the Krebs cycle, oxidative phosphorylation, beta-oxidation, etc.). Plants and nutraceuticals classified under Bio-Intelligence are those that regulate the neuroendocrine and immunological systems and cellular processes, thus controlling the interactions between the various systems in the body. Finally, plants and nutraceuticals classified under Organization are those that relate to the structure and function of specific organs.

Combinations of plants and nutraceuticals from these three classification groups have synergistic effect because they address each necessary component of cellular and organic health—in effect they provide the triangle on which healing is fully supported.

An illustrative example of synergy in medicinal plants is an in vitro study that demonstrates how the activity of herbal Berberine alkaloids is strongly potentiated by the action of 5'-methoxyhydnocarpin (5'-MHC)—an active principle of another phytomedicine (denominated Hydnocarpus wightiana). It shows a strong increase of accumulation of berberine in the cells in the presence of 5'-MHC, indicating that this plant compound effectively disabled the bacterial resistance mechanism against the berberine antimicrobial, thus showing the synergy of both substances. Stermitz F R, et al., Synergy in a medicinal plant: antimicrobial action of berberine potentiated by 5'-methoxyhydnocarpin, a multidrug pump inhibitor. Proc Natl Acad Sci USA. 2000 February; 97:1433-7.

A further demonstration may be provided of synergistic effect on a molecular scale by studying the gene expression profile changes in response to various plant ingredients and combinations thereof. Experiments are already underway demonstrating the expression profile in response to the formulations. We will be aided in this work because researchers have already begun studying the expression profiles of various medicinal plants, thus providing a database of knowledge from which to build. E.g., Gohil, et al., mRNA Expression Profile of a Human Cancer Cell Line in Response to *Ginkgo Biloba* Extract: Induction of Antioxidant Response and the Golgi System, Free Radic Res. 2001; 33:831-849.

Finally there may be further presentation of gene expression results using whole-genome microarray analysis to demonstrate the formulation's capability to provide gene activation (upregulation or downregulation).

What is claimed is:

1. A method of treating Parkinson's disease in a patient in need thereof comprising administering an effective amount of a synergistic nutraceutical composition, wherein said composition comprises: 21 mg of *Eleutherococcus senticosus*, 106 mg of *Panax ginseng*, 32 mg of *Rhodiola rosea*, 4 mg of *Schizandra chinensis*, 106 mg of *Astragalus membranaceus*, 106 mg of *Ganoderma lucidum*, 106 mg of *Uncaria tomentosa*, 21 mg of Coenzyme Q10, 21 mg of *Ginkgo biloba*, 64 mg of *Hydrocotyle asiatica*, 106 mg of *Radix polygalae*, 21 mg of *Silybum marianum*, 4 mg of *Smilax regelii*, 21 mg of *Tabebuia avellanedae*, 106 mg of Vitamin B1 and 106 mg of Vitamin E together with pharmaceutically acceptable excipients to said patient sufficient to alleviate said disease.

* * * * *